US00PP35034P2

(12) United States Plant Patent
Mathey

(10) Patent No.: US PP35,034 P2
(45) Date of Patent: Mar. 14, 2023

(54) ***HYDRANGEA* PLANT NAMED 'SMNHSG'**

(50) Latin Name: *Hydrangea serrata*
Varietal Denomination: SMNHSG

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,052

(22) Filed: Sep. 26, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP28,672 P3 * 11/2017 Wood ..... Plt./250

OTHER PUBLICATIONS

Spring Meadow Nursery Plant Finder p. 34, retrieved on Nov. 2, 2022 at https://springmeadownursery.com/plantfinder/ice/P396, 1-3. (Year: 2022).*
Trademark Electronic Search System (TESS) retrieved on Nov. 2, 2022 at https://tmsearch.uspto.gov/bin/showfield?f=doc&state=4808:4vgax9.3.1, one page. (Year: 2022).*

* cited by examiner

*Primary Examiner* — June Hwu
(74) *Attorney, Agent, or Firm* — C. Anne Whealy

(57) ABSTRACT

A new and distinct cultivar of *Hydrangea* plant named 'SMNHSG', characterized by its upright and outwardly spreading plant habit; moderately vigorous growth habit; strong and sturdy stems; dark green-colored leaves; freely and remontant flowering habit with numerous panicles per plant; showy lacecap inflorescences with purplish red-colored sterile flowers that when "blued" are purple in color; and good garden performance.

3 Drawing Sheets

Figure 1:
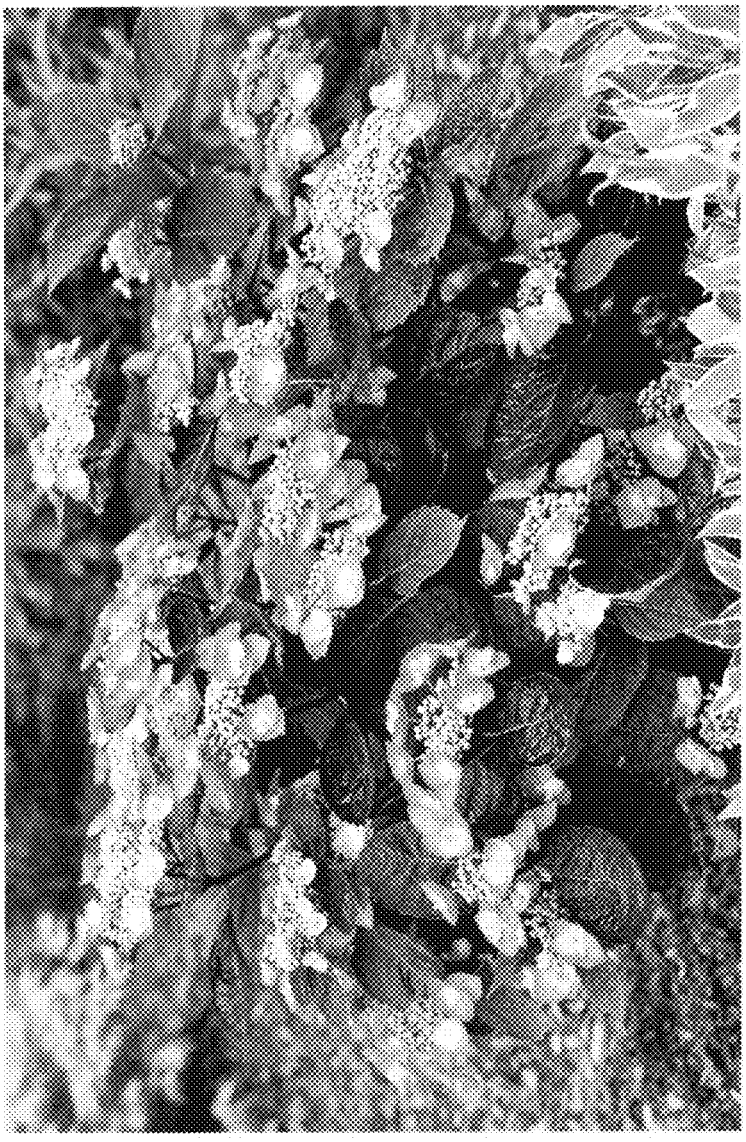

Botanical designation: *Hydrangea serrata.*
Cultivar denomination: 'SMNHSG'.

BACKGROUND OF THE INVENTION

The present invention relates to a new and distinct *Hydrangea* plant, botanically known as *Hydrangea serrata*, commonly referred to as Mountain *Hydrangea* and hereinafter referred to by the name 'SMNHSG'.

The new *Hydrangea* plant is a product of a planned breeding program conducted by the Inventor in Grand Haven, Mich. The objective of the breeding program was to develop new freely and remontant flowering *Hydrangea* plants with strong stems and attractive lacecap inflorescences.

The new *Hydrangea* plant originated from a cross-pollination during the summer of 2016 of *Hydrangea serrata* 'MAK20', disclosed in U.S. Plant Pat. No. 24,820, as the female, or seed parent and *Hydrangea serrata* 'Dariya', not patented, as the male, or pollen, parent. The new *Hydrangea* plant was discovered and selected by the Inventor as a single flowering plant from within the progeny of the stated cross-pollination in a controlled environment in Grand Haven, Mich. during the summer of 2018.

Asexual reproduction of the new *Hydrangea* plant by softwood cuttings in a controlled environment in Grand Haven, Mich. since the summer of 2018 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNHSG'. These characteristics in combination distinguish 'SMNHSG' as a new and distinct *Hydrangea* plant:

1. Upright and outwardly spreading plant habit.
2. Moderately vigorous growth habit.
3. Strong and sturdy stems.
4. Dark green-colored leaves.
5. Freely and remontant flowering habit with numerous panicles per plant.
6. Showy lacecap inflorescences with purplish red-colored sterile flowers that when "blued" are purple in color.
7. Good garden performance.

Plants of the new *Hydrangea* differ from plants of the female parent, 'MAK20', in the following characteristics:

1. Sterile flowers of plants of the new *Hydrangea* have smaller sepals than sterile flowers of plants of 'MAK20'.
2. Sepals of sterile flowers of plants of the new *Hydrangea* are more intense purplish red in color than sepals of sterile flowers of plants of 'MAK20'.

Plants of the new *Hydrangea* differ from plants of the male parent, 'Dariya', primarily in plant habit as plants of the new *Hydrangea* are more uniformly mounded than plants of 'Dariya'.

Plants of the new *Hydrangea* can be compared to plants of *Hydrangea hybrida* 'SMNMAKTSR', disclosed in U.S. Plant Pat. No. 28,672. In side-by-side comparisons, plants of the new *Hydrangea* differed primarily from plants of 'SMNMAKTSR' in the following characteristics:

1. Sterile flowers of plants of the new *Hydrangea* have larger sepals than sterile flowers of plants of 'SMNMAKTSR'.
2. Sepals of sterile flowers of plants of the new *Hydrangea* are purplish red in color whereas sepals of sterile flowers of plants of 'SMNMAKTSR' are darker and more reddish pink in color.
3. Plants of the new *Hydrangea* have a more freely and remontant flowering habit than plants of 'SMNMAKTSR'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) comprises a side perspective view of a typical flowering plant of 'SMNHSG' growing in an outdoor nursery.

Figure 2:
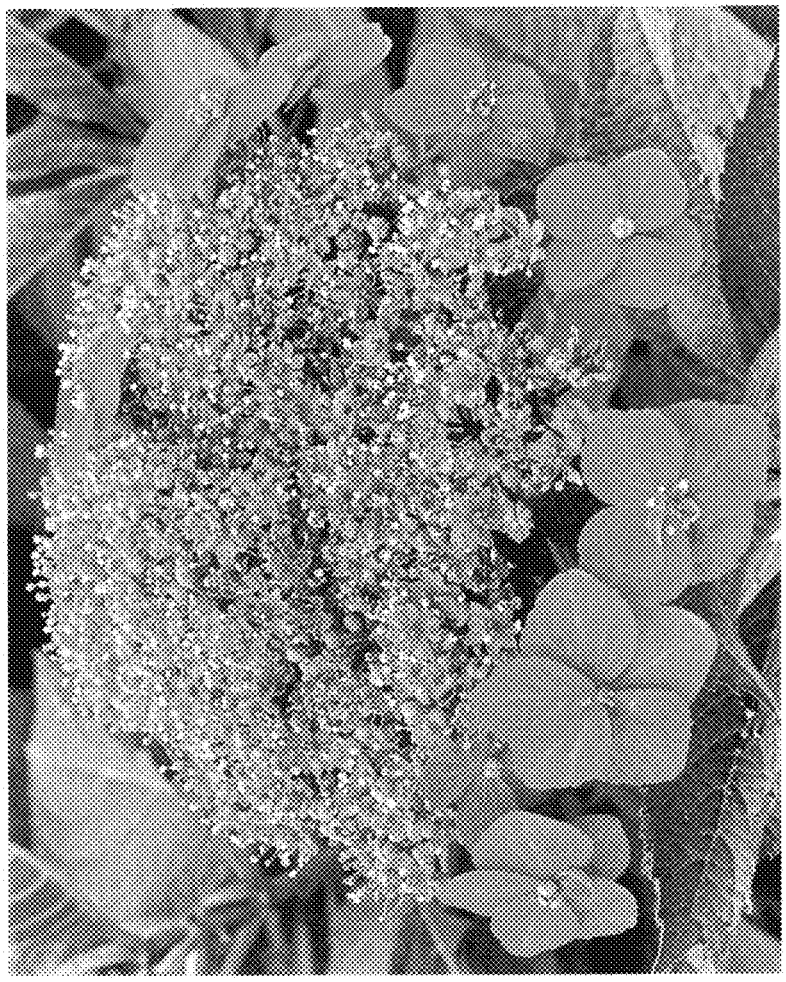

The photograph on the second sheet (FIG. 2) is a close-up view of a typical fully developed inflorescence of 'SMNHSG' that has not been "blued".

Figure 3:
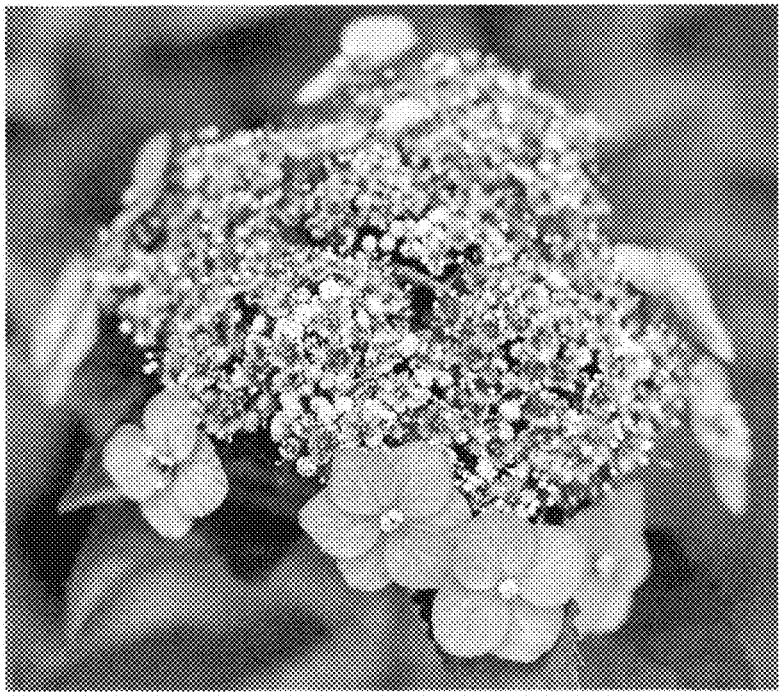

The photograph on the third sheet (FIG. 3) is a close-up view of a typical fully developed inflorescence of 'SMNHSG' that has been "blued".

DETAILED BOTANICAL DESCRIPTION

Plants used for the following description were grown during the summer in three-gallon containers in a polyethylene-covered greenhouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were three years old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea serrata* 'SMNHSG'.

Parentage:

*Female, or seed, parent.*—*Hydrangea serrata* 'MAK20', disclosed in U.S. Plant Pat. No. 24,820.

*Male, or pollen, parent.*—*Hydrangea serrata* 'Dariya', not patented.

Propagation:

*Type cutting.*—By softwood cuttings.

*Time to initiate roots, summer.*—About ten days at temperatures about 20° C.

*Time to produce a rooted young plant, summer.*—About 30 days at temperatures about 20° C.

*Root description.*—Medium in thickness to thick; fibrous and fleshy; typically white in color, actual color of the roots is dependent on substrate composition, water quality, fertilizers, substrate temperature and age of roots.

*Rooting habit.*—Freely to moderately freely branching; medium density.

Plant description:

*Plant form and growth habit.*—Perennial deciduous shrub; upright to outwardly spreading plant habit; broad and uniformly mounded inverted triangle; strong and sturdy lateral branches; freely branching habit with about 40 lateral branches developing per plant; moderately vigorous growth habit and moderate to rapid growth rate.

*Plant height.*—About 30 cm.

*Plant diameter or area of spread.*—About 60 cm.

*Lateral branches.*—Length: About 25 cm. Diameter: About 5 mm. Internode length: About 6 cm. Texture: Initially, slightly pubescent and becoming smooth and glabrous with development. Strength: Strong, sturdy. Aspect: About 45° to 70° from vertical. Color: Close to 144B distally tinged with close to 176A; when woody, close to N200A; lenticels, close to 200B.

Leaf description:

*Arrangement.*—Opposite, simple.

*Length.*—About 6 cm to 11 cm.

*Width.*—About 4 cm to 8 cm.

*Shape.*—Elliptic.

*Apex.*—Acuminate.

*Base.*—Obtuse.

*Margin.*—Serrulate.

*Texture, upper and lower surfaces.*—Glabrous, rugose, coriaceous; prominent venation on lower surface.

*Venation pattern.*—Pinnate.

*Color.*—Developing leaves, upper surface: Close to NN137B. Developing leaves, lower surface: Close to 147B. Fully expanded leaves, upper surface: Close to NN137A; occasionally towards the apex, tinged with close to 200A to 200B; venation, close to 144B tinged with close to 176A. Fully expanded leaves, lower surface: Close to 147B; venation, close to 144B.

*Petioles.*—Length: About 5 mm. Diameter: About 2 mm. Texture, upper and lower surfaces: Slightly pubescent. Color, upper surface: Close to 144B tinged with close to 176A. Color, lower surface: Close to 144B.

Inflorescence & flower description:

*Flower type and habit.*—Single sterile and fertile flowers arranged on relatively flat lacecap umbels; flowers face upright to somewhat outwardly depending on position on the umbel.

*Fragrance.*—None detected.

*Natural flowering season.*—Continuous and remontant flowering habit from June to August in Grand Haven, Mich.

*Quantity of flowers.*—Freely flowering habit; about 200 to 300 fertile flowers and about eight to ten sterile flowers develop per inflorescence.

*Inflorescence height.*—About 4 cm.

*Inflorescence diameter.*—About 8 cm.

*Flower diameter, fertile flowers*.—About 7 mm.

*Flower depth* (*height*), *fertile flowers*.—About 5 mm.

*Flower diameter, sterile flowers*.—About 4.5 cm.

*Flower depth* (*height*), *sterile flowers*.—About 1 cm.

*Flower buds, fertile flowers*.—Length: About 3 mm. Diameter: About 4 mm. Shape: Obovate. Color: Close to 144D.

*Flower buds, sterile flowers*.—Length: About 3 mm. Diameter: About 4 mm. Shape: Obovate. Color: Close to 144D.

*Petals, fertile flowers*.—Arrangement: About five to nine in one to two whorls. Length: About 5 mm. Width: About 2 mm. Shape: Elliptic. Apex: Acute. Base: Truncate. Margin: Entire. Texture, upper and lower surfaces: Smooth, glabrous. Color: When opening, upper and lower surfaces: Close to 62B; when "blued", close to 98A. Fully opened, upper and lower surfaces: Close to 62B; when "blued", close to 98A.

*Petals, sterile flowers*.—Arrangement: About five to seven in a single whorl. Length: About 3 mm. Width: About 2 mm. Shape: Narrowly elliptic. Apex: Acute. Base: Obtuse. Margin: Entire. Texture, upper and lower surfaces: Smooth, glabrous. Color: When opening, upper and lower surfaces: Close to 62B; when "blued", close to 98A. Fully opened, upper and lower surfaces: Close to 62B; when "blued", close to 98A.

*Sepals, fertile flowers*.—Quantity per flower: Five fused at the base in a single whorl. Length: About 1 mm. Width: About 1 mm. Shape: Orbicular. Apex: Obtuse. Margin: Entire. Texture, upper and lower surfaces: Smooth, glabrous. Color: When opening, upper and lower surfaces: Close to 144D; when "blued", close to 144D. Fully opened, upper and lower surfaces: Close to 144D; when "blued", close to 144D.

*Sepals, sterile flowers*.—Quantity per flower: Five in a single whorl. Length: About 2.5 cm. Width: About 2.5 cm. Shape: Ovate. Apex: Acute. Base: Cordate. Margin: Serrulate to entire. Texture, upper and lower surfaces: Slightly rugose, glabrous with pronounced midvein on lower surface. Color: When opening, upper surface: Close to 144D and distally, close to 63A; when "blued", close to 144D and distally, close to N82A to N82B. When opening, lower surface: Close to 144D and distally, close to 63C; when "blued", close to 144D and distally, close to 84C. Fully opened, upper surface: Close to 63B; when "blued", close to N82A to N82B; color does not change with subsequent development. Fully opened, lower surface: Close to 63D; when "blued", close to 84C; color does not change with subsequent development.

*Pedicels, fertile flowers*.—Length: About 5 mm. Diameter: About 1 mm. Angle: About 45° from peduncle axis. Strength: Strong, flexible. Texture: Smooth, glabrous. Color: Close to 63C; when "blued", close to 90A.

*Pedicels, sterile flowers*.—Length: About 1 cm. Diameter: About 2 mm. Angle: About 30° from peduncle axis. Strength: Strong, flexible. Texture: Slightly pubescent. Color: Close to 63C; when "blued", close to 90A and proximally, close to 83A.

*Reproductive organs, fertile flowers*.—Stamens: Quantity per flower: About twelve. Filament length: About 4 mm. Filament color: Close to 70B; when "blued", close to 98A. Anther shape: Oblong. Anther length: About 1 mm. Anther color: Close to N77B; when "blued", close to 98A. Pollen amount: Scarce. Pollen color: Close to N155A. Pistils: Pistil quantity per flower: One. Pistil length: About 3 mm. Stigma shape: Three to four-lobed. Stigma color: Close to 64B; when "blued", close to 94A. Style length: About 1 mm. Style color: Close to 64B; when "blued", close to 94A.

*Reproductive organs, sterile flowers*.—Stamens: Quantity per flower: About ten. Filament length: About 3 mm. Filament color: Close to 70B; when "blued", close to 98A. Anther shape: Oblong. Anther length: About 1 mm. Anther color: Close to N77B; when "blued", close to 98A. Pollen amount: Scarce. Pollen color: Close to N155A. Pistils: Pistil quantity per flower: One. Pistil length: About 2 mm. Stigma shape: Three-lobed. Stigma color: Close to 64B; when "blued", close to 94A. Style length: About 1 mm. Style color: Close to 64B; when "blued", close to 94A.

*Seeds and fruits*.—Seed and fruit development has not been observed on plants of the new *Hydrangea*.

Pathogen & pest resistance: To date, plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind and to tolerate temperatures ranging from about −25° C. to about 37° C.

It is claimed:

1. A new and distinct *Hydrangea* plant named 'SMNHSG' as illustrated and described.

* * * * *